United States Patent [19]
Vallier

[11] Patent Number: 5,885,550
[45] Date of Patent: Mar. 23, 1999

[54] OPHTHALMIC WHITENING SOLUTION

[76] Inventor: Deandra K. Vallier, 1101 Sherman Ave., Hood River, Oreg. 97031

[21] Appl. No.: 109,480

[22] Filed: Jul. 2, 1998

[51] Int. Cl.[6] .................................................. A61K 49/00
[52] U.S. Cl. ........................ 424/10.32; 424/10.3; 514/912
[58] Field of Search ............................... 424/10.3, 10.32; 514/912

[56] References Cited

U.S. PATENT DOCUMENTS

| | | | |
|---|---|---|---|
| 3,598,833 | 8/1971 | Hiltmann et al. | 260/307 |
| 3,758,686 | 9/1973 | Sieger et al. | 424/241 |
| 4,350,676 | 9/1982 | Laties et al. | 424/7 |
| 4,419,352 | 12/1983 | Cox et al. | 424/248.4 |
| 4,587,257 | 5/1986 | Desantis et al. | 514/392 |
| 4,783,444 | 11/1988 | Watkins et al. | 514/19 |
| 4,839,175 | 6/1989 | Guo et al. | 424/450 |
| 4,866,049 | 9/1989 | Maumenee et al. | 514/169 |
| 5,151,440 | 9/1992 | Gluchowski | 514/377 |
| 5,180,721 | 1/1993 | Burke | 514/213 |
| 5,585,354 | 12/1996 | Ohashi et al. | 514/12 |
| 5,683,993 | 11/1997 | Tsao | 514/108 |

*Primary Examiner*—Zohreh Fay

[57] ABSTRACT

The invention consists of an aqueous ophthalmic solution comprising a particular amount of blue or bluish dye which increases the apparent whiteness of the sclera, or the white portion of the eyeball.

8 Claims, No Drawings

OPHTHALMIC WHITENING SOLUTION

BACKGROUND OF THE INVENTION

1. Field of the Invention

This invention constitutes the addition of a blue dye or other blueing agent to aqueous ophthalmic solutions, generally available, to give the apparent effect of increased whiteness to the eyes.

Vasoconstrictors such as naphazoline hydrochloride and tetrahydrozoline hydrochloride are currently being used to relieve redness of the eye and have been in use for sometime. The effectiveness of ophthalmic solutions containing these vasoconstrictors, however, are dramatically improved in their ability to increase the whiteness of the sclera when blueing agents are added thereto. Moreover, current ophthalmic solutions which do not contain any vasoconstrictors whatsoever also become effective in increasing the whiteness of the eye when combined with the instant invention.

2. Description of the Related Art

Substantially all whiteness formulas used at present assess a white color sample as all the whiter, the lighter and bluer it actually is. See, E. Ganz, "*Whiteness Formulas: A Selection,*" Applied Optics, vol. 18, No. 7, at page 1073 (1979). For instance, it is a common practice to use a blue dye as a whitening agent in detergents due to a mechanism in which a yellow cast in the fabrics is covered by the blue dye. [See, Example 1, Cahn and Lynn, Jr., "*Encyclopedia of Chemical Technology*," Third Ed., Vol. 22, John Wiley & Sons, Inc., New York, N.Y., 1983, at page 399.] Similarly, the same mechanism (addition of blue dyes or pigments) is being used in the plastic industry to mask the yellowing of the plastics upon exposure to gamma-ray sterilization.

The present invention is based on applying this mechanism to the eye. Application of eye drops to the eyeball causes the lower well of the bottom eyelid to fill with the aqueous solution. The normal process of blinking causes the top eyelid to pull the solution from the lower well up and across the surface of the entire eyeball as it opens, increasing the apparent whiteness of the sclera portion of the eye.

DISCLOSURE OF THE INVENTION

This invention comprises an aqueous ophthalmic solution containing a particular amount of blue or bluish dye which is pharmaceutically acceptable for ophthalmic use, preferably FD&C Blue No. 1, in order to increase the apparent whiteness and/or brightness of the sclera, or white portion of the eyeball. In addition, the ophthalmic solution of the invention may include vasoconstrictors and conventional and well-known pharmaceutically acceptable demulcents, antihistamines, preservatives, stabilizing agents, buffering agents and tonicity adjusters.

A vasoconstrictor is used for the relief of redness of the eye due to minor eye irritations. Demulcents are used for the temporary relief of burning and irritation due to dryness of the eye, for the temporary relief of discomfort due to minor irritation of the eye or to exposure to wind or sun, and as a lubricant to prevent further irritation of the eye. Antihistamines are used to relieve minor eye symptoms of itchy, watery eyes due to hay fever, ragweed, pollen, grass, and animal hair and dander. Preservatives (anti-microbial agents) are used for a multi-dose package in order to preserve the solution from microbial growth. A commonly used anti-microbial agent for ophthalmic solutions includes benzalkonium chloride. However, some patients are sensitive to the preservative. For these patients a preservative-free formulation is preferably used and such formulation is packaged in a single or daily dose container. The tonicity of the ophthalmic solution of the invention is adjusted to isotonic or slightly hypotonic for dry eye conditions. The pH of the ophthalmic solution of the invention is adjusted to approximately 4–8, preferably 6.5–7.5 to minimize the temporary irritation of the eye due to the instillation of the solution.

It is an object of the invention to provide an ophthalmic solution which gives the appearance of whitening and/or brightening the sclera, the white portion of the eye.

It is still another important object of the invention to provide a blue dye or blueing agent which is added to conventionally available ophthalmic solutions.

It is still another important object of the invention to provide an ophthalmic solution additive comprising a particular amount of blue or bluish dye.

It is still another important, more specific object of the invention to provide an ophthalmic solution of a conventional type having as an additive FD&C Blue No. 1.

It is still another important, more specific object of the invention to provide an ophthalmic solution additive which is principally the disodium salt of ethyl [4-[p-[ethyl (m-sulfobenzyl) amino]-α-(o-sulfophenyl) benzylidene[-2,5-cyclohexadien-1-ylidene] (m-sulfobenzyl) ammonium hydroxide inner salt plus p-sulfobenzyl and o-sulfobenzyl salts.

DESCRIPTION OF THE PREFERRED EMBODIMENT(S)

The invention relates to the color additive FD&C Blue No. 1, which is principally the disodium salt of ethyl [4-[p-[ethyl (m-sulfobenzyl) amino]-α-(o-sulfophenyl) benzylidene[-2,5-cyclohexadien-1-ylidene] (m-sulfobenzyl) ammonium hydroxide inner salt plus p-sulfobenzyl and o-sulfobenzyl salts, and which is currently approved by the FDA as a color additive for drugs intended for use in or around the area of the eyes.

Indeed, FD&C Blue No. 1, is available from such companies as Hilton-Davis Co., 3M, BASF, Toman, Evergreen, and Spectrum Chemical. The FD&C Blue No. 1 color additive is further described by the government authorities as (a) Identity. (1) The color additive FD&C Blue No. 1 is principally the disodium salt of ethyl [4-[p-[ethyl (m-sulfobenzyl) amino]-α-(o-sulfophenyl) benzylidene]-2,5 -cyclohexadien-1-ylidene] (m-sulfobenzyl) ammonium hydroxide inner salt with smaller amounts of the isomeric disodium salts of ethyl [4-[p-[ethyl (p-sulfobenzyl) amino]-α-(o-sulfophenyl) benzylidene]-2,5-cyclohexadien-1-ylidene] (p-sulfobenzyl) ammonium hydroxide inner salt and ethyl [4-[p-[ethyl (o-sulfobenzyl) amino]-α-(o-sulfophenyl) benzylidene]-2,5 -cyclohexadien-1-ylidene] (o-sulfobenzyl) ammonium hydroxide inner salt.

While FD&C Blue No. 1 is the preferred agent, any blue dye or bluish agent will effectively give the desired result.

Thus, in the practice of the invention, it is only necessary to add a particular amount s of blue color dye or other blueing agent which would be inert and not cause any discomfort or reaction with the organic tissues of the eye, and yet, gives the whitening effect that is desired.

In the practice of the invention, the dye may range from 0.00005% to 0.01%, by weight percent by volume of the ophthalmic solution. That is, the percentages expressed are weight percents of the overall ophthalmic solution. It is found that having a concentration of 0.002% gives the optimum effect with respect to whitening the sclera.

In order to establish the efficacy of the invention, a number of solutions were made and tested. All of the results of the tested solutions were subjectively and visually interpreted. In each instance the solutions comprising the blue dye or blueing agents in the aforementioned amounts resulted in an apparent whitening of the sclera portion of the eyes of the test subjects.

The following non-limiting examples illustrate certain aspects of the present invention. All percentages are by weight/volume of the solution.

EXAMPLE 1

A sample of FD&C Blue No. 1 (Hilton Davis, purity: 91%) was dissolved in distilled water at various concentrations and the absorbance at 630 nm was determined with a spectrophotometer. The results are shown in Table 1. It was determined by the vast majority of test subjects that the optimum blue tint was obtained when the absorbance was from approximately 1 to approximately 2.5.

TABLE 1

Concentration and Absorbance

| Concentration of FD&C Blue No. 1 | Absorbance at 630 nm |
|---|---|
| 0.00005% | 0.075 |
| 0.0001% | 0.147 |
| 0.00025% | 0.348 |
| 0.0005% | 0.720 |
| 0.00075% | 1.089 |
| 0.001% | 1.429 |
| 0.002% | 2.518 |
| 0.003% | 2.743 |
| 0.01% | 2.927 |

EXAMPLE 2

The interaction between FD&C Blue No. 1 and benzalkonium chloride (BAC) was studied. Aqueous solutions containing 0.01% benzalkonium chloride and 0.001–0.01% of FD&C Blue No. 1 were prepared. The change of absorbance at 630 mn was followed, while the solutions were kept in the dark at ambient temperature. The results (Table 2) shows that the blue color faded due to the interaction with benzalkonium chloride initially, but the absorbance would plateau when the initial concentration of the dye was sufficient.

TABLE 2

Absorbance Change of FD&C Blue No. 1 in the Presence of Benzalkonium chloride

| | Absorbance at 630 nm | | | |
|---|---|---|---|---|
| Time (day) | 0.001% Dye | 0.003% Dye | 0.005% Dye | 0.01% Dye |
| 0 | 0.931 | 2.589 | 3.248 | 4.580 |
| 1 | 0.754 | 1.633 | 2.499 | 2.908 |
| 6 | 0.507 | 0.972 | — | — |
| 8 | — | — | 1.869 | 2.838 |
| 9 | — | 0.854 | — | — |
| 11 | — | — | 1.828 | 2.815 |
| 12 | — | 0.780 | — | — |

EXAMPLE 3

Ophtalmic sample solutions were prepared by dissolving 0.012% of naphazoline hydrochloride, 0.2% of glycerin, 0.01% of BAC, 0/1% of edetate disodium, 0.99% of boric acid, 0.17% of sodium borate decahydrate, 0.23% of sodium chloride and 0.001%–0.006% of FD&C Blue No. 1 in distilled water. The absorbance at 630 nm was followed, while the solutions were kept in the dark at ambient temperature. The results are summarized in Table 3.

TABLE 3

Absorbance of Ophthalmic Solutions

| | Absorbance at 630 mn | | |
|---|---|---|---|
| Time (day) | 0.001% Dye | 0.005% Dye | 0.006% Dye |
| 0 | 0.924 | 3.254 | 3.312 |
| 1 | 0.719 | 2.706 | 2.809 |
| 8 | 0.537 | 2.603 | 2.748 |
| 15 | — | 2.514 | 2.707 |
| 20 | 0.366 | — | — |
| 23 | — | 2.428 | 2.715 |
| 36 | 0.252 | — | — |

EXAMPLE 4

An ophthalmic solution was prepared by dissolving 0.012% of naphazoline hydrochloride, 0.2% of glycerin, 0.1% of edetate disodium, 0.99% of boric acid, 0.17% of sodium borate decahydrate, 0.12% of sodium chloride and 0.001% of FD&C Blue No. 1 in distilled water. The solution was kept in the dark at ambient temperature. The absorbance at 630 nm was 1.439, 1.442, 1.461, and 1.462 at the time of 0, 5, 13, and 33 days, respectively. This example shows that the blue dye in the ophthalmic solution does not fade when BAC is not added to the solution.

While the invention has been disclosed with specific particularity, those of ordinary skill in the art will at once recognize that the concentration of different blue dyes may be utilized—all without departing from the spirit and scope of the invention, and all such changes and modifications are intended to be covered by the appended claims.

What is claimed is:

1. In an aqueous ophthalmic solution, the improvement which comprises the addition of a blueing agent.

2. The improvement in accordance with claim 1, wherein said blueing agent is FD&C Blue No. 1.

3. The improvement in accordance with claim 2, wherein the concentration of FD&C Blue No. 1 is within the range of 0.00005% to 0.01% by weight percent by volume of the solution.

4. The improvement in accordance with claim 3, wherein the concentration of FD&C Blue No. 1 is about 0.002 weight percent by volume of the solution.

5. The method of treating the eyes of mammals which comprises administering an aqueous ophthalmic solution containing a blueing agent that has the effect of whitening or brightening the sclera portion of the eyeball.

6. The method in accordance with claim 5, wherein said blueing agent comprises FD&C Blue No. 1.

7. The method in accordance with claim 6, wherein the concentration of said FD&C Blue No. 1 is within the range of 0.005 weight percent by volume to 0.01%.

8. The method in accordance with claim 7, wherein the concentration of FD&C Blue No. 1 is 0.002%.

* * * * *